US006773892B1

(12) United States Patent
Deth

(10) Patent No.: US 6,773,892 B1
(45) Date of Patent: Aug. 10, 2004

(54) METHODS OF IDENTIFYING AND DETERMINING THE EFFECTIVENESS OF THERAPEUTIC PROCESSES OR AGENTS FOR THE TREATMENT OF SCHIZOPHRENIA AND RELATED DISORDERS

(75) Inventor: Richard C. Deth, Waban, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 09/550,103

(22) Filed: Apr. 14, 2000

Related U.S. Application Data

(62) Division of application No. 08/833,703, filed on Apr. 8, 1997, now Pat. No. 6,080,549.

(51) Int. Cl.$^{7}$ ...................... G01N 33/53; G01N 33/567; G01N 1/30; G01N 33/566; C12Q 1/16

(52) U.S. Cl. ......................... 435/7.2; 435/7.21; 435/35; 435/40.5; 436/501; 436/503; 436/504

(58) Field of Search ................................ 435/7.2, 7.21, 435/40.5, 35, 503; 436/501, 504, 71, 804, 811

(56) References Cited

U.S. PATENT DOCUMENTS 6,080,549 A * 6/2000 Deth

OTHER PUBLICATIONS

Deth, et al, 1996, Biol. Psychiatry, 39: 504–510.*

Sharma, et al., 1999, Mol. Psychiartry, 4:235–246.*

* cited by examiner

*Primary Examiner*—Elizabeth Kemmerer
*Assistant Examiner*—Sandra Wegert
(74) *Attorney, Agent, or Firm*—Weingarten, Schurgin, Gagnebin & Lebovici LLP

(57) ABSTRACT

Methods for detecting schizophrenia or related neuropsychiatric disorders based on modifications of the contribution of the $D_4$ receptor to phospholipid methylation levels are described herein. Individuals with schizophrenia or related neuropsychiatric disorders have a deficiency in phospholipid methylation activity compared with normal individuals. Methods for screening therapeutic processes or agents for use in treatment of schizophrenia or related neuropsychiatric disorders are also described.

5 Claims, 4 Drawing Sheets

METHODS OF IDENTIFYING AND DETERMINING THE EFFECTIVENESS OF THERAPEUTIC PROCESSES OR AGENTS FOR THE TREATMENT OF SCHIZOPHRENIA AND RELATED DISORDERS

CROSS REFERENCE TO RELATED APPLICATIONS

This application is a divisional of U.S. application Ser. No. 08/833,703 filed Apr. 8, 1997, now U.S. Pat. No. 6,080,549, entitled METHODS AND MATERIALS FOR THE DIAGNOSIS AND TREATMENT OF SCHIZOPHRENIA AND RELATED DISORDERS; the whole of which is hereby incorporated by reference herein.

BACKGROUND OF THE INVENTION

Schizophrenia is a devastating neuropsychiatric disorder which affects approximately 1% of the population and results in serious disruption in the lives of afflicted individuals and their families. Common symptoms include delusions, conceptual disorganizations and visual or auditory hallucinations, as well as changes in affective behavior. A number of scales for the rating of symptoms and methods for ascertaining the diagnosis have been developed, including the DSM classification by the American Psychiatric Association (Diagnostic and Statistical Manual of Mental Disorders (4th edition), pp. 273–316, 1994), which have attempted to refine the accuracy of clinical diagnosis. However, it is likely that similar symptoms can result from several underlying abnormalities, and diagnosis relying solely on clinical symptoms is difficult and controversial, as well as subjective, time-consuming and costly.

The cause or causes of schizophrenia remain obscure. A defect in dopamine pathways of synaptic neuronal function is a central feature of the most widely held etiopathogenic theory (known as the Dopamine Hypothesis), with recent emphasis on the role of $D_4$-type dopamine receptors (Taubes, Science 265:1034–1035, 1994). However, studies to date have failed to identify abnormalities in the basic receptor structure, suggesting that dysfunction may result from an alteration in the dynamic regulation of receptor activity.

Dopamine receptors are members of a large superfamily of G protein-coupled receptors which share a high degree of structural similarity while recognizing a widely divergent array of substances which affect cellular function. Recent advances in the study of these receptors, including the development of 3-dimensional structural models (Teeter et al., J. Med. Chem. 37:2874–2888, 1994), have led to the identification of key locations on the receptors which can modulate their function and which therefore may be sites of malfunction in schizophrenia (Samama et al., J. Biol. Chem. 268:4625–4636, 1993). One such critical location or "hot spot" in the dopamine $D_4$ receptor is a methionine amino acid residue (Van Tol et al., Nature 350:610–614, 1991).

A number of clinical and metabolic studies have documented altered methionine metabolism in individuals with schizophrenia (Kelsoe et al., J. Neurosci. Res. 8:99–103, 1982; Ismail et al., Biol. Psych. 13:649–660, 1978; Sargent et al., Biol. Psych. 32:1078–1090, 1992). For example, the administration of methionine has been shown to elicit an acute psychotic reaction in persons with schizophrenia but lacks such an effect in normal individuals (Cohen et al., Biol. Psych. 8:209–225, 1974). Conversely, administration of S-adenosylmethionine has been shown to have antidepressant benefits (Kemali et al., Biochemical and Pharmacological Roles of Adenosylmethionine and the Central Nervous System, Pergamon Press, pp. 141–147, 1979).

Recently, these findings have been integrated upon the discovery that methionine residue #313 (human $D_4$ receptor numbering) of the dopamine $D_4$ receptor appears to be abnormally modified in schizophrenic individuals (Deth, "Compositions and Methods for Detection of Schizophrenia," WO 96/37780, the whole of which is hereby incorporated by reference herein). Methionine residue #313 is normally modified by the addition of an adenosyl group to its sulfur atom via the action of a methionine adenosyltransferase (MAT) enzyme; however, individuals with schizophrenia are known to be deficient in MAT activity (Carl et al., Biol. Psych. 13:773–776, 1978) and, thus, are expected to possess a lesser amount of the modified form of the dopamine $D_4$ receptor. This deficiency is evident in a variety of tissues, including brain tissue and blood cells, particularly white blood cells, and is central to the biochemical diagnosis of schizophrenia.

BRIEF SUMMARY OF THE INVENTION

This invention is based upon the discovery that a biochemical abnormality in phospholipid methylation associated with schizophrenia is linked to the abnormal modification of the dopamine $D_4$ receptor and the clinical manifestations of altered dopamine neurotransmission. This discovery provides novel and empirical approaches for the diagnosis and treatment of schizophrenia and other related disorders.

This invention pertains to novel biochemical methods for assisting in the diagnosis of schizophrenia and other neuropsychiatric disorders, including, but not limited to, schizoaffective disorders, depression and dementias. The method of the present invention is based on the fact that dopamine receptor function is abnormal in individuals with schizophrenia, and upon the discoveries, described herein, that the dopamine $D_4$ receptor is a direct participant in the methylation of membrane phospholipids and that phospholipid methylation is abnormally altered in schizophrenic individuals. Consequently, an altered membrane fluidity may play a significant role in producing the symptoms of schizophrenia.

In one embodiment of the present invention, the level of phospholipid methylation in a tissue sample, e.g., peripheral blood cells (such as lymphocytes), from an individual to be tested is measured, preferably using [$^{14}$C]formic acid labelling or any similar method of labelling the methylfolate pool. Additionally, the level of contribution of the $D_4$ receptor to phospholipid methylation in the same sample is also determined. The measured levels are then compared with corresponding levels of the same indicators from a tissue sample of a normal individual; a lower level of phospholipid methylation activity in the tested individual compared with the normal individual is indicative of schizophrenia or a related neuropsychiatric disorder in the tested individual.

A lower level of $D_4$ receptor contribution to phospholipid methylation activity in the tested individual compared with the normal individual is indicative of schizophrenia specifically in the tested individual. Alternatively, a [$^3$H]-methylmethionine based method of phospholipid methylation activity determination is used, a more indirect assay.

This invention also pertains to novel methods for identifying therapeutic processes or agents for treatment of schizophrenia or related neuropsychiatric disorders using cultured cell lines transfected with the $D_4$ receptor gene. Processes or agents identified by the methods described herein can increase the amount of phospholipid methylation to the normal level.

Furthermore, this invention also pertains to novel methods for determining the effectiveness of therapeutic processes or agents for treatment of neuropsychiatric disorders, and in particular schizophrenia. In one embodiment of the invention, the effectiveness of a therapeutic process or agent can be assessed by making an initial determination of the level of phospholipid methylation in a lymphocyte sample from an individual to be tested, administering the process or agent to be assessed, and making a subsequent determination of the level of phospholipid methylation in the lymphocyte sample from the individual. The corresponding levels of phospholipid methylation can be compared; an increase in the level of phospholipid methylation (preferably a normalization of methylation levels) indicates that the process or agent is effective for treating schizophrenia.

In a particular embodiment, the determination of the levels of phospholipid methylation is carried out using [$^{14}C$] formic acid labelling of the methylfolate pool. Thus, the present invention has utility for the identification of agents and processes for use in the treatment of schizophrenia, and such agents, processes and drugs are also the subject of this invention.

Any tissues which display the schizophrenia-associated alterations in methionine metabolism are suitable for use in the methods of the present invention. Such tissues include brain tissue and red and white blood cells. Peripheral blood cells (especially lymphocytes) are particularly useful in the present invention because of their accessibility, allowing the methods of the present invention to be carried out on a blood sample from the individual, and because lymphocyte membranes contain the $D_4$receptor.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
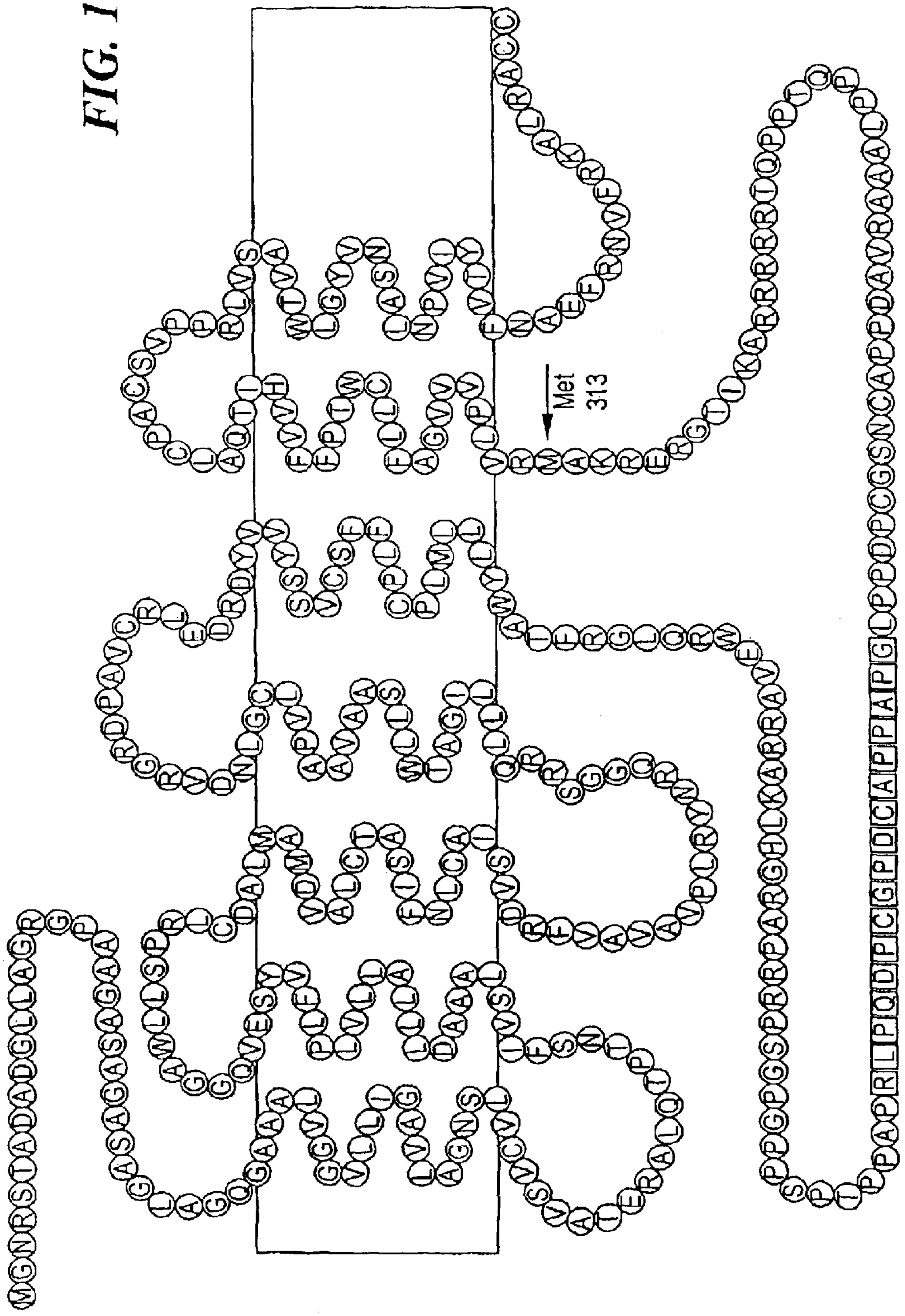
FIG. 1 is a prior art rendering of the dopamine $D_4$ receptor structure, shown the amino acid sequence (SEQ ID NO: 1) of the human dopamine $D_4$ receptor and its proposed seven transmembrane helical elements (Deth, WO 96/37780). The cell membrane is shown as a rectangle with the extracellular surface at the top and intracellular surface at the bottom. Methionine #313 (the "hot spot") is indicated with an arrow.

The "Dopamine Hypothesis" is the most widely held biochemical explanation for the etiology of schizophrenia and theorizes a defect in dopamine pathways of synaptic neuronal function, with recent emphasis on the role of $D_4$-type dopamine receptors. Dopamine receptors are members of the superfamily of G protein-coupled receptors. All G protein-coupled receptors share the basic structural motif of seven transmembrane-spanning helices, formed as the single polypeptide chain traverses the plasma membrane (O'Dowd, J. Neurochem 60:804–816, 1993). In the case of the dopamine receptor, the neurotransmitter dopamine diffuses into the central core of the receptor on the outer surface of the cell where critical amino acid residues provide specific recognition. The binding of dopamine and its recognition by the receptor cause an alteration in the conformation of the receptor, and this "active" conformation conveys the neurotransmitter signal to GTP-binding G proteins located on the inner surface of the cell membrane.

Five subtypes of dopamine receptors have been identified, designated as $D_1$, $D_2$, $D_3$, $D_4$ and $D_5$. Based upon functional and structural similarities, the $D_1$ and $D_5$ receptors form a $D_1$-like receptor group, and the $D_2$, $D_3$ and $D_4$ receptors comprise a $D_2$-like group. Among dopamine receptors, the $D_1$-like receptors primarily complex with and activate the G protein $G_5$, while the $D_2$-like receptors activate the $G_1$ and/or $G_0$ proteins. The potency of neuroleptic drugs in treating schizophrenia has been found to be closely correlated with their antagonism of the $D_2$-like receptors (Seeman et al., Proc. Nat. Acad. Sci. USA 72:4376–4380, 1975), and antagonism of the $D_4$ receptor subtype provides a better correlation than do the $D_2$ or $D_3$ subtypes, implicating the $D_4$ receptor as the most likely target of neuroleptic drugs (Seeman and van Tol, Trends Pharmacol Sci. 15:264–270, 1994).

Generally, a receptor must be occupied by its agonist or partial agonist in order to attain its active conformation and convey the neurotransmitter signal. However, in a phenomenon known as "spontaneous receptor activity," it is possible for a receptor to maintain the active conformation even in the absence of agonist occupation, although the extent of this phenomenon appears to be dependent upon prior exposure of the cells to the appropriate agonist.

Without wishing to be bound by theory, the binding of the agonist apparently induces a conformational change in the receptor, causing it to become active. In this active state, a modifiable amino acid residue (a "hot spot") on the intracellular portion of the receptor, exactly 18 residues (5 helical turns) from the agonist binding site, becomes accessible to a native enzyme. This enzyme modifies the "hot spot" such that the modification (typically a phosphorylation in other spontaneously active receptors but adenosylation in the $D_4$ receptor) prevents the receptor from returning to the inactive conformation upon departure of the agonist. In fact, the receptor remains in the active conformation and continues to propagate the neurotransmitter signal, until the modification is removed by subsequent enzyme activity.

The dopamine $D_4$ receptor, methionine #313 (human $D_4$ receptor numbering) has been identified as such a "hot spot"; that is, referring to FIG. 1, methionine #313 is a modifiable amino acid residue on the intracellular portion of the $D_4$ receptor, located 18 residues (exactly 5 helical turns) below the key residue which is utilized by agonists to induce the active receptor conformation (Deth, "Compositions and Methods for Detecting Schizophrenia," WO 96/37780).

It has been shown that any modification of residues occupying the same position as dopamine $D_4$ receptor methionine #313 in other receptors will cause the receptor to become spontaneously active and exhibit spontaneous activity (Samama et al., J. Bio. Chem. 268:4625–4636, 1993).

Similarly, it is believed that the binding of dopamine to the $D_4$ receptor causes an alteration of the receptor conformation to the active conformation. As a result of this alteration, methionine #313 becomes accessible to MAT, and MAT adds an adenosyl group to the sulfur atom of the methionine. This modification of methionine #313 by MAT prevents the re-configuration of the receptor to the inactive form upon departure of the agonist. Thus, the dopamine $D_4$ receptor is capable of spontaneously maintaining its active conformation, i.e., maintaining its active conformation without dopamine occupation. This active conformation is maintained until the modification (e.g., the adenosyl group) is removed by subsequent enzyme activity.

While phosphorylated threonine residues can be restored to their native state by the action of phosphatase enzymes, the fate of S-adenosylated methionine residue #313 was not immediately obvious. However, by analogy to S-adenosylmethionine, it was considered that the terminal methyl group may be available for donation in a methyltransferase reaction. The location of the "hot spot" residue is at the cytoplasmic surface of the plasma membrane, and it is thus located at or near the head groups of membrane phospholipids, raising the possibility that the S-adenosylated form of the $D_4$ receptor might serve as a donor of methyl groups for methylation of the phospholipid phosphatidylethanolamine (PE) in the stepwise synthesis of phosphatidylcholine (PC).

Phosphatidylethanolamine (PE) is sequentially N-methylated by the action of two enzymes, phospholipid methyltransferases I and II (PLMT I and II), located on the inner and outer sides of the plasma membrane respectively (Hirata et al., Science 209:1082, 1980). Formation of N-monomethyl PE by PLMT I has been linked to the control of the membrane microviscosity, with increased formation leading to decreased microviscosity (i.e., increased membrane fluidity). To determine whether $D_4$ receptors might play a role in phospholipid methylation, CHO cells transfected with human $D_4$ receptor were incubated with $[^3H]$-methyl-methionine for 1 hr. in the presence or absence of dopaminergic ligands and GTP, followed by extraction of phospholipids and determination of $[^3H]$ incorporation. The basal level of phospholipid methylation, however, could be augmented by about 30% by addition of a combination of GTP(1 mM) and dopamine (10 $\mu$M). The inclusion of the dopamine antagonists haloperidol (1 $\mu$M) (or clozapine) produced a decrease in phospholipid methylation to a level which was approximately 75% below the original basal level. In studies with PC12 cells, haloperidol treatment caused a similar decrease in phospholipid methylation, suggesting that dopamine receptor-dependent phospholipid methylation may be a feature of a number of cell types, including neuronal tissues.

An impairment in methylation reactions has previously been suggested to accompany and to cause schizophrenia. In an early hypothesis ("the transmethylation hypothesis"), a defect resulting in the formation of hallucinogens was proposed. Later, the "one-carbon hypothesis" suggested a defect in biochemical pathways involving methionine, S-adenosylmethionine and folic acid. To determine whether $D_4$ receptor-dependent phospholipid methylation was altered in individuals with schizophrenia, males ages 27–70 with well documented schizophrenia by DSM-IV criteria, were studied and compared with normal controls. Lymphocytes were incubated for 1 hr. in $[^3H]$ methionine in the presence and absence of a combination of dopamine (10 $\mu$M) and GTP (1 $\mu$M) with and without haloperidol (1 $\mu$M). Basal phospholipid methylation was approximately 3.5-fold lower in the patient samples, indicating a profound defect in this pathway. Dopamine/GTP stimulated methylation by an average of 30% in controls and by 165% in patients. Haloperidol inhibition reached 25% below basal in controls and 39% below basal in patients. The results confirm the presence of a defect in one-carbon metabolism in schizophrenia and show that this defect is remarkably prominent in the phospholipid methylation pathway involving the dopamine $D_4$ receptor. Consequently, an altered membrane fluidity, in the composition of cell membranes such as nerve membranes, appears to play a significant role in producing the symptoms of schizophrenia.

Figure 2:
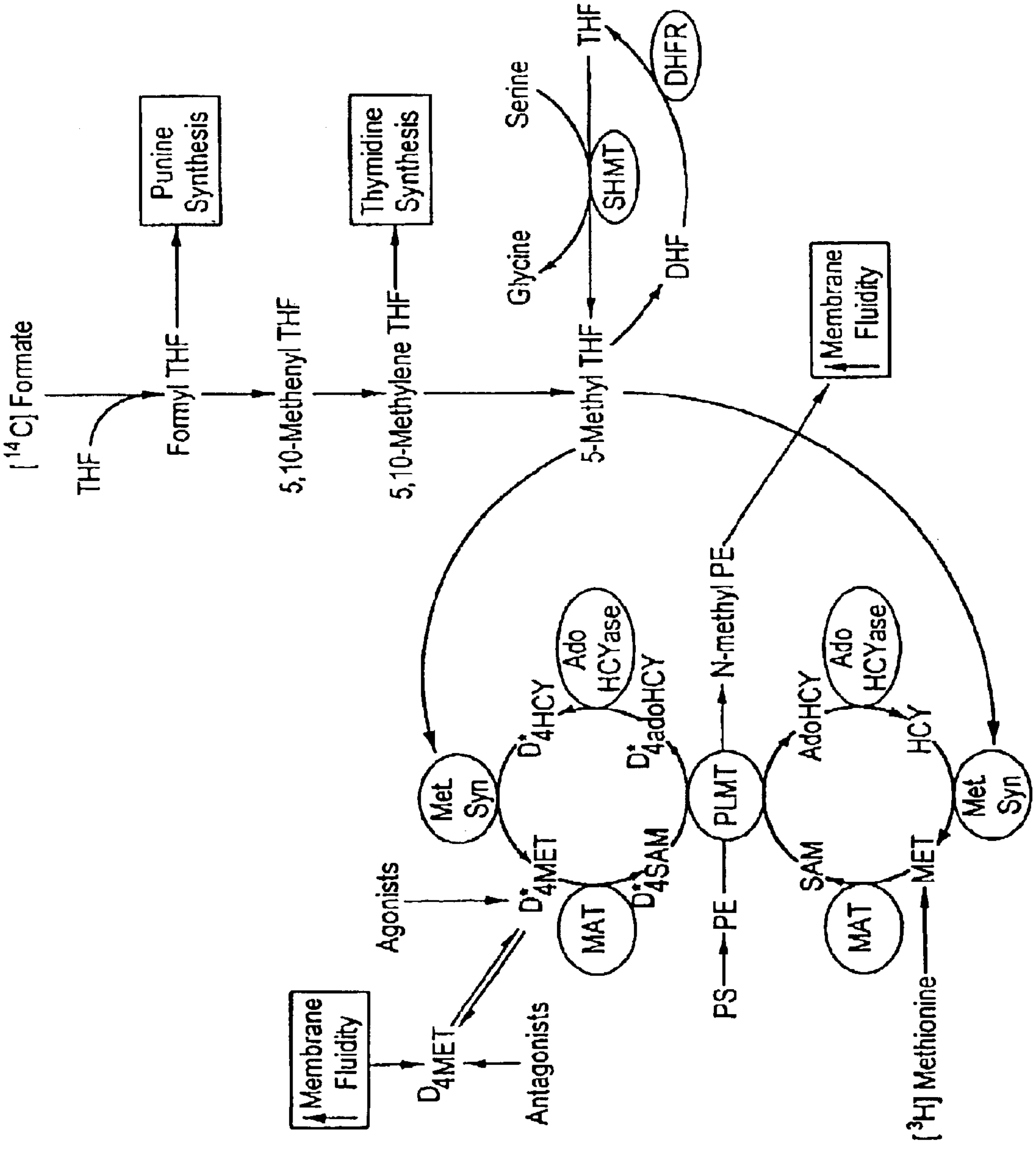
FIG. 2 is a schematic outline of metabolic pathways showing the use of [$^{14}C$] formic acid or [$^3H$] methionine to measure $D_4$ receptor-dependent and receptor-independent phospholipid methylation.

By placing these observations in the context of those made in earlier investigations of methionine metabolism, it is possible to formulate a unified "phospholipid methylation hypothesis" which combines the dopamine hypothesis of schizophrenia with the previously postulated theories of a defect in single carbon metabolism. Referring to FIG. 2, PLMT I-mediated N-methylation of PE is the initial step in phospholipid methylation. The $D_4{}^*{}_{SAM}$ form of dopamine $D_4$ receptors can now be recognized to play a significant role as a source of methyl groups for this reaction while SAM itself presumably provides the additional receptor-independent source. As shown in the lower portion of the figure, the classical methionine cycle provides for methyl donation to phospholipid methyltransferase I (PLMT I) by formation of S-adenosylmethionine via the action of methionine adenosyltransferase (MAT). After methyl transfer, adenosylhomocysteine hydrolase (Ado Hcyase) removes the adenosyl moiety from adenosylhomocysteine and methionine is reformed via the action of methionine synthase (Met Synthase) to complete the cycle. Methionine synthase utilizes cobalamin (Vit $B_{12}$) to effect the methylation of homocysteine, with 5-methyl tetrahydrofolate (5-methyl THF) serving as the primary methyl donor. Serine hydroxymethyltransferase (Serine HMT) forms 5,10-methylene THF from the conversion of serine to glycine. The active R* form of the dopamine $D_4$ receptor ($D_4{}^*{}_{MET}$) is adenosylated at M313 by MAT to yield $D_4{}^*{}_{SAM}$ which can serve as a donor of methyl groups for N-methylation of PE by PLMT I. The remainder of the $D_4$ cycle is hypothesized to involve the actions of AdoHcyase and Met Synthase. Binding of negative antagonists to the inactive $D_4$ state of the receptor can serve to reduce its participation in phospholipid methylation. As a transmembrane protein, the $D_4$ receptor may be conformationally sensitive to changes in membrane fluidity, creating the potential for negative feedback regulation.

Clearly the net amount of PE methylation will depend upon three factors: 1) the concentration of the substrate PE; 2) availability of the methyl donors SAM and $D_4{}^*{}_{SAM}$; and 3) the catalytic activity provided by PLMT I. Availability of $D_4{}^*{}_{SAM}$ is dependent upon a number of factors including the density of $D_4$ receptors and the prevailing level of the $D_4{}^*{}_{MET}$ state. Both SAM and $D_4{}^*{}_{SAM}$ are dependent upon MAT activity and the efficiency of those events which allow for restoration of the methionine form of the receptor after methyl donation, some of which are outlined in FIG. 2. In short, the dynamics of the methionine cycle of methyl donation determine the ability of both SAM and the $D_4$ receptor to supply methyl groups for phospholipid methylation.

The following examples are presented to illustrate the advantages of the present invention and to assist one of ordinary skill in making and using the same. These examples are not intended in any way otherwise to limit the scope of the disclosure.

EXAMPLE I

Involvement of a $D_4$ Dopamine Receptor in Phospholipid Methylation

Figure 3A:
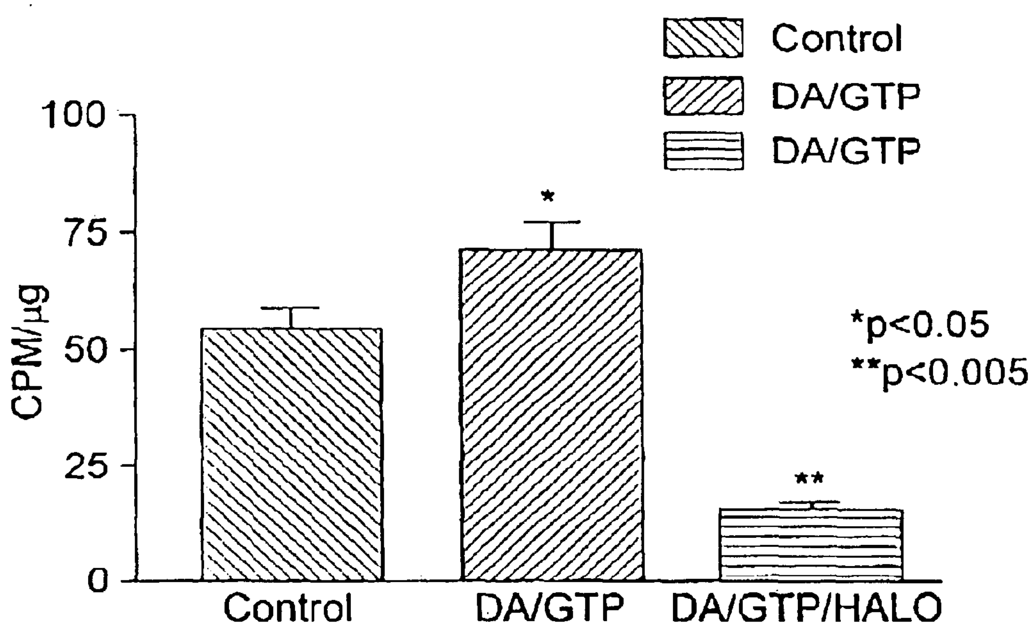
FIGS. 3*a*, 3*b* and 3*c* show involvement of $D_4$ dopamine receptor in phospholipid methylation.
Figure 3B:
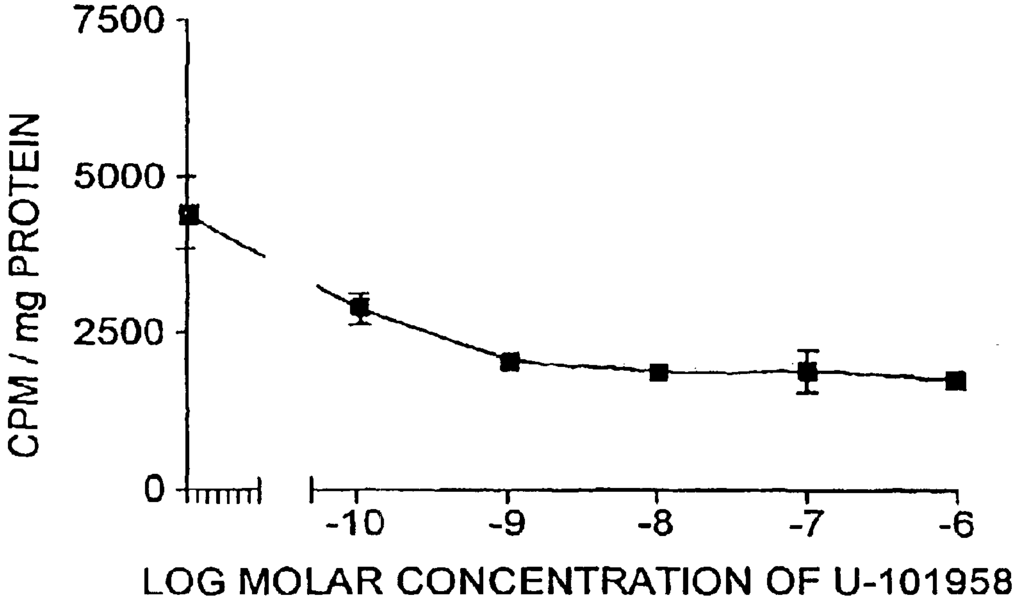
Figure 3C:
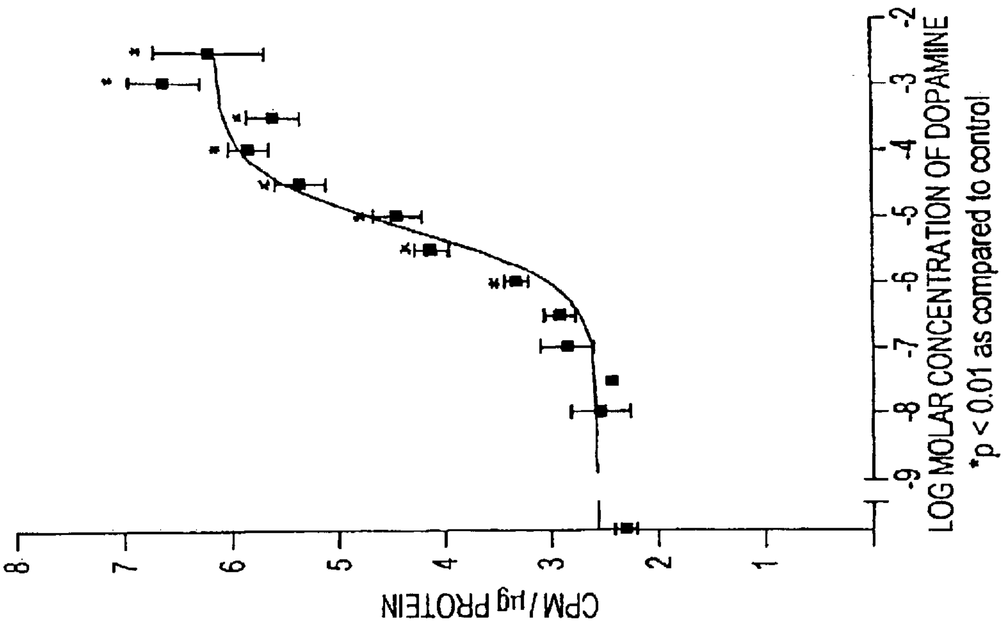

Incorporation of [$^3$H] label into phospholipids was measured in intact CHO cells transfected with the $D_4$ receptor gene (CHO/$D_4$ cells) after incubation with [$^3$H-methyl] methionine. The media of cells growing in monolayer was changed to 1 ml of Hank's balanced salt solution, nucleoside free, containing 8 $\mu$Ci/ml [$^3$H-methyl] methionine. After a 60 min incubation, 1.5 ml of ice-cold 10% trichloroacetic acid (TCA) was added, and cells were harvested and centrifuged. The pellet was washed with 2.5 ml of TCA and extracted with 15 ml of a 6:3:1 mixture of $CHCl_3$/$CH_3OH$/HCl (2 M). The $CHCl_3$ phase was washed twice with 4 ml of 0.1 M KCl in 50% $CH_3OH$, and an aliquot of the phospholipid-containing $CHCl_3$ was dried and counted. The graph depicted in FIG. 3*a* shows cells treated with either vehicle (Control), the $D_4$receptor-selective agonists GTP (1 mM) and dopamine (10 $\mu$M) (DA/GTP) or both GTP and dopamine plus the $D_4$ receptor-selective antagonist haloperidol (1 $\mu$M) (HALO) at the start of [$^3$H-methyl]methionine incubation. A small stimulation of phospholipid methylation by the agonists GTP and dopamine and a large inhibition when the antagonist haloperidol is simultaneously included was observed. FIG. 3*b* shows dose-dependent inhibition of [$^{14}$C] formate-labelled phospholipid methylation in CHO/$D_4$ cells grown in nucleoside-free medium by the highly $D_4$-selective antagonist U-101,958. FIG. 3*c* shows dose-dependent dopamine stimulation of [$^{14}$C] formate-labelled phospholipid methylation in SK-N-MC cells, which are derived from a human neuroblastoma and naturally contain the $D_4$ receptor, grown in the presence of nucleosides.

Referring again to FIG. 3*b,* dose-response studies in CHO cells with the $D_4$ receptor-selective antagonist U-101,958 conducted in the absence of agonist indicated that its inhibitory effects occurred at concentrations consistent with occupation of dopamine $D_4$ receptors, with an $IC_{50}$ of 0.2 nM as compared to its reported $K_D$ of 1 nM (Schlacter et al., Soc. Neurosci. Abstr. 21:252.7, 1995). Similar results were obtained with another $D_4^-$ selective antagonist L-745,870. This inhibition verifies that spontaneous activity of the $D_4$ receptor does indeed play an important role in phospholipid methylation, especially under nucleoside free growth conditions. The magnitude of antagonist effects suggest that the $D_4$ receptor can serve as a significant source of methyl groups, supplemented by a dopamine antagonist-insensitive component which likely represents the contribution of S-adenosyl methionine itself.

EXAMPLE II

Phospholipid Methylation in Lymphocytes from Persons with Schizophrenia vs. Normal Controls To determine whether $D_4$ receptor-dependent phospholipid methylation was altered in schizophrenia, the labelling of phospholipids by [$^3$H]-methyl-methionine in lymphocytes obtained from people with schizophrenia (as defined by DSM IV diagnostic criteria *Diagnostic and Statistical Manual of Mental Disorders* (4th Edition), American Psychiatric Association, Washington, D.C., 1987, pp. 759–764) under medical treatment) was measured as compared to lymphocytes from healthy controls. Lymphocytes were isolated as previously described (De La Rosa et al., J. Biol. Chem. 267:10699, 1992) and aliquots of 4×10$^6$ cells were resuspended in Hank's balanced salt solution containing 8 $\mu$Ci/ml [$^3$H-methyl]methionine for 60 min. Dopamine (10 $\mu$M) and GTP (1 mM) with or without haloperidol (1 $\mu$M) were added to additional groups. Incorporation of [$^3$H-methyl] label into phospholipids was determined as described in Example I.

Figure 4A:
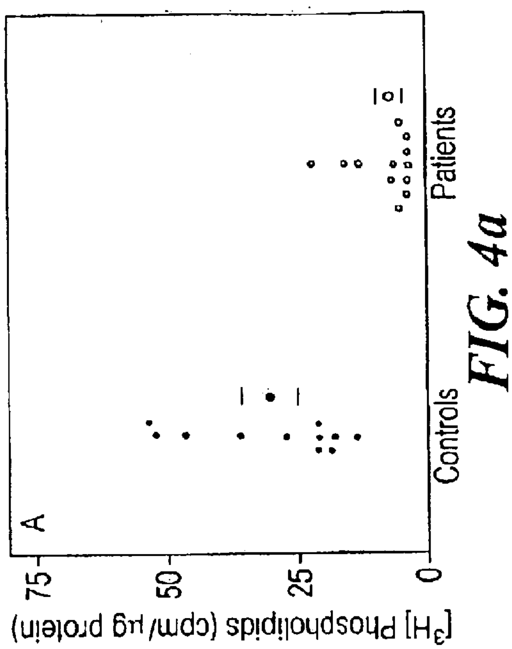
FIGS. 4*a* and 4*b* show phospholipid methylation in lymphocytes from persons with schizophrenia vs. normal controls.
Figure 4B:
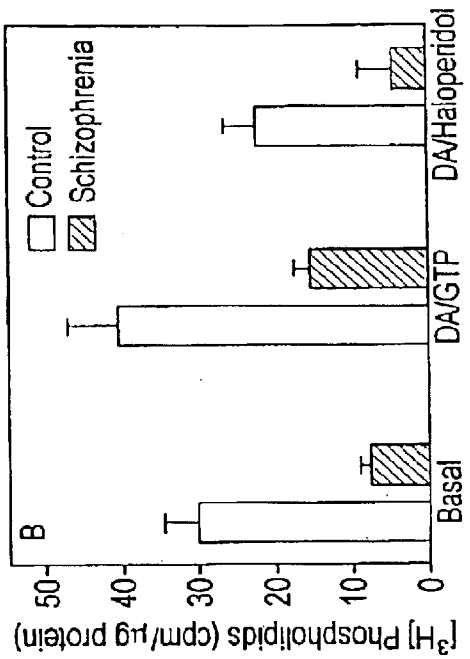

(A) Individual basal levels of phospholipid methylation and their mean =/− SEM. (B) Influence of dopamine/GTP and haloperidol on phospholipid methylation in control and schizophrenia samples. Differences between control and patient values are significant ($p<0.001$) for all treatment groups. The mean basal level of phospholipid methylation in patient samples was less than one-third the value of controls, indicating a major deficit in this process (FIG. 4A). In both groups, the addition of dopamine and GTP caused a significant increase in methyl incorporation while haloperidol caused a significant decrease (FIG. 4B), but the percentage changes in control were less than had been observed in CHO cells. However, these effects were relatively exaggerated in patient lymphocytes, associated with their low initial values. The difference between the agonist-stimulated and antagonist-inhibited values, which can be considered as the potential contribution dopamine receptors can make to this process, was only 20% smaller in the schizophrenia group. Thus while $D_4$ dopamine receptors are important in determining the level of phospholipid methylation in isolated lymphocytes, especially in individuals with schizophrenia, the large deficiency in schizophrenia appears to involve aspects other than the receptor contribution per se.

MATERIALS AND METHODS

Materials

U-101,958 maleate and L-745,870 hydrochloride, two examples of $D_4$ receptor-selective antagonists, were purchased from Research Biochemicals International (Natick, Mass.). [$^{14}$C]-formic acid was obtained from American Radiolabeled Chemicals Inc. (St. Louis, Mo.).

Cell Preparations

CHO cells transfected with the $D_4$ receptor gene were fed with minimum essential medium (alpha modifications, with or without nucleosides) (pH 7.2) containing 2 mM L-glutamine, W/G418 antibiotic (400 mg/L), donor horse serum (2.5%), fetal bovine serum (2.5%), penicillin/streptomycin/fungizone (1%), $CuSO_4$ ($10^{-6}$M). Cells (200,000 cells/well) were plated in 6-well- plates and placed in 5% $CO_2$ incubator at 37° C.

Phospholid Methylation Assay

Two-day-old confluent, cultured $D_4$-transfected CHO cells were used for assay. The pH of Hank's balanced buffer (HBSS) was adjusted to pH 7.4 using sodium bicarbonate buffer. [$^{14}$C]-formic acid (1 $\mu$Ci/ml) and pharmacological agents were added to HBSS. Feeding medium was removed from the well and then 600 $\mu$l of the HBSS solution with the radiolabelled formic acid (warmed to 37° C.) was added to each well of 6-well-plates. Plates were incubated at 37° C. for 30 minutes in the culture incubator. The reaction was stopped by washing once with ice-cold PBS (pH 7.4) and, after aspirating off the HBSS, 500 $\mu$l of 10% trichloroacetic acid (TCA) was added. Cells were harvested by scraping with a cell scraper and transferred into a plastic microcentrifuge tube. Another 500 $\mu$l of TCA was added to rinse and transferred into the same tube. A sample (100 $\mu$l) was taken out for Lowry protein assay after the cells were homogenized. Each tube was spun in a bench top minifuge at 12,000 rpm for 15 minutes. After the TCA supernatant was aspirated off, 2N HCl (150 $\mu$l) and 100% methanol (450 $\mu$l) were added to each tube. The pellets were homogenized and 900 $\mu$l of chloroform ($CHCl_3$) was added to each tube. The sample tubes were placed on a shaker for 1 hour at room temperature to allow for phase separation and the top aqueous layer was removed by aspiration after shaking. 0.1 M KCl in 50% methanol (500 $\mu$l) was then added and the top aqueous layer was carefully removed by aspiration after thorough vortexing. The $CHCl_3$ layer was saved for scintillation counting. 300 μl of the $CHCl_3$ layer was transferred to a counting vial and evaporated to dryness by a heated water bath. Six replicate values were obtained for each experimental group. CPM values were normalized to the protein content of each sample and expressed as the mean +/− S.E.M. for the group. Differences between groups were analyzed by a t-test with $p<0.05$ as the criterion for significance.

Use

The metabolic relationships described herein have been used to develop methods of identifying therapeutic processes or agents for treating schizophrenia or a related neuropsychiatric disorder. These screening methods include establishing a cultured cell line, either naturally expressing $D_4$ receptor or transfected with the $D_4$ receptor gene, as an assay system; making an initial determination of the level of phospholipid methylation in the cultured cells; administering the candidate therapeutic process or agent to be assessed to the cultured cell assay system; and determining the level of phospholipid methylation following introduction of the candidate process or agent. An increase in the level of phospholipid methylation subsequent to administration of the candidate therapeutic process or agent indicates that the candidate process or agent is potentially therapeutically effective for treating schizophrenia or a related neuropsychiatric disorder. The particular influence of the candidate therapeutic process or agent on $D_4$ receptor-dependent phospholipid methylation is assessed by a comparison of agonist stimulated VS. antagonist-inhibited methylation levels. An increase in the receptor component indicates a potentially useful effect on dopamine function in the brain.

A similar method can be used to assess the effectiveness of the therapeutic process or agent for treating schizophrenia or a related neuropsychiatric disorder in a patient.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by definitions contained in the appended claims and equivalents thereof.

What is claimed is:

1. A method of identifying an agent for treating schizophrenia or a related neuropsychiatric disorder wherein said related neuropsychiatric disorder has the feature of involving modification of dopamine D4 receptor-linked phospholipid methylation and wherein said method comprises the steps of:

(a) establishing an assay system comprising a cultured cell line, said cultured cell line either naturally expressing D4 receptors or transfected with the D4 receptor gene;

(b) making an initial determination of the level of phospholipid methylation in cells of said cell line;

(c) administering to cells of said cell line the candidate agent to be assessed, (d) making a subsequent determination of the level of phospholipid methylation in cells of said cell line; and (e) comparing the corresponding levels of phospholipid-methylation from steps (b) and (d), wherein an increase in the level of phospholipid methylation subsequent to administration of the candidate agent indicates that the agent is potentially therapeutically effective for treating schizophrenia or said related neuropsychiatric disorder.

2. The method of claim 1, further including, prior to step (e), the step of determining the level of phospholipid methylation in the presence or absence of added $D_4$ receptor agonists and/or antagonists.

3. The method of claim 1, wherein the determination of the level of phospholipid methylation is carried out by labelling of the methylfolate pool.

4. The method of claim 2, wherein the level of phospholipid methylation is determined by labelling the methylfolate pool with $[^{14}C]$-formic acid.

5. The method of claim 1, wherein steps (c), (d) and (e) are carried out more than once.

* * * * *

UNITED STATES PATENT AND TRADEMARK OFFICE

CERTIFICATE OF CORRECTION

PATENT NO. : 6,773,892 B1 
DATED : August 10, 2004
INVENTOR(S) : Richard C. Deth It is certified that error appears in the above-identified patent and that said Letters Patent is hereby corrected as shown below:

Column 4,
Line 21, "$G_5$" should read -- $G_s$ --;

Column 10,
After line 2, please insert the Sequence Listing as follows:

SEQUENCE LISTING

<110> Deth, Richard C.

<120> METHODS OF IDENTIFYING AND DETERMINING THE EFFECTIVENESS OF THERAPEUTIC PROCESSES OR AGENTS FOR THE TREATMENT OF SCHIZOPHRENIA AND RELATED DISORDERS

<130> NU-431AX

<140> 09/550,103
<141> 2000-04-14

<150> 08/833,703
<151> 1997-08-08

<160> 1

<170> FastSEQ for Windows Version 4.0

<210> 1
<211> 387
<212> PRT
<213> Homo sapien

UNITED STATES PATENT AND TRADEMARK OFFICE
CERTIFICATE OF CORRECTION

PATENT NO. : 6,773,892 B1 
DATED : August 10, 2004
INVENTOR(S) : Richard C. Deth It is certified that error appears in the above-identified patent and that said Letters Patent is hereby corrected as shown below:

Column 10 (cont'd),

```
<400> 1
Met Gly Asn Arg Ser Thr Ala Asp Ala Asp Gly Leu Leu Ala Gly Arg
 1               5                  10                  15
Gly Pro Ala Ala Gly Ala Ser Ala Gly Ala Ser Ala Gly Leu Ala Gly
            20                  25                  30
Gln Gly Ala Ala Ala Leu Val Gly Gly Val Leu Leu Ile Gly Ala Val
        35                  40                  45
Leu Ala Gly Asn Ser Leu Val Cys Val Ser Val Ala Thr Glu Arg Ala
    50                  55                  60
Leu Gln Thr Pro Thr Asn Ser Phe Ile Val Ser Leu Ala Ala Ala Asp
65                  70                  75                  80
Leu Leu Leu Ala Leu Leu Val Leu Pro Leu Phe Val Tyr Ser Glu Val
                85                  90                  95
Gln Gly Gly Ala Trp Leu Leu Ser Pro Arg Leu Cys Asp Ala Leu Met
            100                 105                 110
Ala Met Asp Val Ala Leu Cys Thr Ala Ser Ile Phe Asn Leu Cys Ala
        115                 120                 125
Ile Ser Val Asp Arg Phe Val Ala Val Ala Val Pro Leu Arg Tyr Asn
    130                 135                 140
Arg Gln Gly Gly Ser Arg Arg Gln Leu Leu Leu Ile Gly Ala Thr Trp
145                 150                 155                 160
Leu Leu Ser Ala Ala Val Ala Ala Pro Val Leu Cys Gly Leu Asn Asp
                165                 170                 175
Val Arg Gly Arg Asp Pro Ala Val Cys Arg Leu Glu Asp Arg Asp Tyr
            180                 185                 190
Val Val Tyr Ser Ser Val Cys Ser Phe Phe Leu Pro Cys Pro Leu Met
        195                 200                 205
Leu Leu Leu Tyr Trp Ala Thr Phe Arg Gly Leu Gln Arg Trp Glu Val
```

UNITED STATES PATENT AND TRADEMARK OFFICE

CERTIFICATE OF CORRECTION

PATENT NO. : 6,773,892 B1

DATED : August 10, 2004

INVENTOR(S) : Richard C. Deth

It is certified that error appears in the above-identified patent and that said Letters Patent is hereby corrected as shown below:

Column 10 (cont'd),

```
    210                     215                     220
Ala Arg Arg Ala Lys Leu His Gly Arg Ala Pro Arg Arg Pro Ser Gly
225                 230                 235                 240
Pro Gly Pro Pro Ser Pro Thr Pro Pro Ala Pro Arg Leu Pro Gln Asp
                245                 250                 255
Pro Cys Gly Pro Asp Cys Ala Pro Pro Ala Pro Gly Leu Pro Pro Asp
            260                 265                 270
Pro Cys Gly Ser Asn Cys Ala Pro Pro Asp Ala Val Arg Ala Ala Ala
        275                 280                 285
Leu Pro Pro Gln Thr Pro Pro Gln Thr Arg Arg Arg Arg Arg Ala Lys
    290                 295                 300
Ile Thr Gly Arg Glu Arg Lys Ala Met Arg Val Leu Pro Val Val Val
305                 310                 315                 320
Gly Ala Phe Leu Leu Cys Trp Thr Pro Phe Phe Val Val His Ile Thr
                325                 330                 335
Gln Ala Leu Cys Pro Ala Cys Ser Val Pro Pro Arg Leu Val Ser Ala
            340                 345                 350
Val Thr Trp Leu Gly Tyr Val Asn Ser Ala Leu Asn Pro Val Ile Tyr
        355                 360                 365
Thr Val Phe Asn Ala Glu Phe Arg Asn Val Phe Arg Lys Ala Leu Arg
    370                 375                 380
Ala Cys Cys
385
```

UNITED STATES PATENT AND TRADEMARK OFFICE

CERTIFICATE OF CORRECTION

PATENT NO. : 6,773,892 B1
DATED : August 10, 2004
INVENTOR(S) : Richard C. Deth

It is certified that error appears in the above-identified patent and that said Letters Patent is hereby corrected as shown below:

Column 10 (cont'd),
Line 4, please insert new claim 1 as follows:

--A method of identifying an agent for treating schizophrenia or a related neuropsychiatric disorder wherein said related neuropsychiatric disorder has the feature of involving modification of dopamine D4 receptor-linked phospholipid methylation and wherein said method comprises the steps of:

(a) establishing an assay system comprising a cultured cell line, said cultured cell line either naturally expressing D4 receptors or transfected with the D4 receptor gene;

(b) making an initial determination of the level of phospholipid methylation in cells of said cell line;

(c) administering to cells of said cell line the candidate agent to be assessed;

(d) making a subsequent determination of the level of phospholipid methylation in cells of said cell line; and (e) comparing the corresponding levels of phospholipid methylation from steps (b) and (d), wherein an increase in the level of phospholipid methylation subsequent to administration of the candidate agent indicates that the agent is potentially therapeutically effective for treating schizophrenia or said related neuropsychiatric disorder.--.

Signed and Sealed this

Twenty-seventh Day of September, 2005

JON W. DUDAS
*Director of the United States Patent and Trademark Office*